United States Patent
McGowan

(10) Patent No.: US 10,912,806 B2
(45) Date of Patent: Feb. 9, 2021

(54) COMPOSITION COMPRISING AN ESSENTIAL OIL AND ITS PACKAGING THEREOF

(71) Applicant: Michael McGowan, San Jose, CA (US)

(72) Inventor: Michael McGowan, San Jose, CA (US)

(*) Notice: Subject to any disclaimer, the term of this patent is extended or adjusted under 35 U.S.C. 154(b) by 0 days.

(21) Appl. No.: 16/143,342

(22) Filed: Sep. 26, 2018

(65) Prior Publication Data

US 2020/0093875 A1 Mar. 26, 2020

(51) Int. Cl.
*A61K 36/185* (2006.01)
*A61F 6/00* (2006.01)
*A61K 31/352* (2006.01)
*A61K 9/00* (2006.01)
*A61F 6/04* (2006.01)

(52) U.S. Cl.
CPC ............ *A61K 36/185* (2013.01); *A61F 6/005* (2013.01); *A61K 9/0014* (2013.01); *A61K 31/352* (2013.01); *A61F 6/04* (2013.01)

(58) Field of Classification Search
CPC .. A61K 36/185; A61K 9/0014; A61K 31/352; A61F 6/005; A61F 6/04
USPC ........................................................ 206/69
See application file for complete search history.

(56) References Cited

U.S. PATENT DOCUMENTS

| | | | |
|---|---|---|---|
| 4,446,860 A | 5/1984 | Gutnick | |
| 4,578,379 A | 3/1986 | Cormier | |
| 4,601,714 A | 7/1986 | Burnhill | |
| 4,922,928 A | 5/1990 | Burnhill | |
| 5,467,781 A | 11/1995 | Kato | |
| 6,194,400 B1 | 2/2001 | Nefkens et al. | |
| 6,523,540 B1 | 2/2003 | Harrison | |
| 6,740,333 B2 | 5/2004 | Beckett et al. | |
| 6,742,521 B2 * | 6/2004 | McCleskey | A61F 6/005 128/842 |
| 7,086,403 B2 | 8/2006 | Harrison et al. | |
| 8,303,969 B2 | 11/2012 | Chuah et al. | |
| 8,980,942 B2 | 3/2015 | Stinchcomb et al. | |

(Continued)

FOREIGN PATENT DOCUMENTS

CH 693504 A5 9/2003
WO WO 03/080043 A1 10/2003

OTHER PUBLICATIONS

Foria, Copyright 2018 Flordia Pleasure, https://foriapleasure.com/.

(Continued)

*Primary Examiner* — Jacob K Ackun
(74) *Attorney, Agent, or Firm* — Intellectual Property Law Group LLP

(57) ABSTRACT

There is a composition comprising an essential oil, namely a cannabis essential oil that is compatible with a prophylactic such as a condom. The cannabis essential oil comprises an active ingredient, tetrahydrocannabinol, which heightens the sensation and causes a euphoric feeling during intimate relations. There is a kit allowing for easy access to both the essential oil and condom that comprises two chambers, one chamber for storing the essential oil and the second chamber for storing the condom. The two chambers are easily separable by tearing along the perforated portion. There is a packet comprising two separable chambers for storing the composition comprising the essential oil and a prophylactic.

10 Claims, 2 Drawing Sheets

(56) References Cited

U.S. PATENT DOCUMENTS

| | | |
|---|---|---|
| 10,064,905 B1 * | 9/2018 | Jenn .................. A61K 9/48 |
| 2003/0078303 A1 | 4/2003 | Young et al. |
| 2003/0232101 A1 | 12/2003 | Travis |
| 2005/0045497 A1 * | 3/2005 | Sample ............... A61F 6/005 |
| | | 206/69 |
| 2007/0175484 A1 | 8/2007 | Staab |
| 2007/0181134 A1 | 8/2007 | Lang |
| 2010/0263675 A1 | 10/2010 | Chuah et al. |
| 2013/0281523 A1 | 10/2013 | Letendre et al. |
| 2014/0174961 A1 * | 6/2014 | Lee .................... A61F 6/005 |
| | | 206/69 |
| 2017/0105946 A1 * | 4/2017 | Stepovich ........... A61K 31/05 |
| 2017/0246120 A9 | 8/2017 | Stepovich |
| 2017/0367875 A1 | 12/2017 | Sinai et al. |
| 2018/0360894 A1 * | 12/2018 | Jenn ................. A61K 36/185 |
| 2018/0360896 A1 * | 12/2018 | Jenn ................. A61K 36/185 |

OTHER PUBLICATIONS

International Search Report, dated Nov. 20, 2019, for corresponding International Application No. PCT/US2019/050893, pp. 1-2.
Written Opinion of the International Searching Authority, dated Nov. 20, 2019, for corresponding International Application No. PCT/US2019/050893, pp. 1-5.

* cited by examiner

COMPOSITION COMPRISING AN ESSENTIAL OIL AND ITS PACKAGING THEREOF

BACKGROUND OF THE INVENTION

1. Field of the Invention

The present invention relates to a composition and its packaging thereof; more particularly the present invention relates to a prophylactic compatible, lubricant and stimulant comprising of an essential oil.

2. Background

Some prophylactics such as condoms (male or female) are not compatible with essential oils. More particularly, the essential oil comprising cannabis and the cannabis' stimulant is not compatible with prophylactics such as condoms; these condoms can be male or female condoms. There are condoms that are pre-lubricated; however, the amount of lubricant on the condom is minimal. Typically, there is no need for extra lubricant when the condom is already pre-lubricated. Further, lubricant used with latex condoms/prophylactics does not contain any essential oils nor does it contain an essential oil stimulant. An essential oil base lubricant should not be used with a condom combo because when oil interacts with latex, it weakens the latex and can possibly create holes in the condom.

An essential oil is a natural oil typically obtained from plants, possessing the odor and characteristics of the plant. One of these characteristics is the plant's healing properties. The *Cannabis* plant contains a variety of cannabinoids. One type of cannabinoid is tetrahydrocannabinol ("THC") which is extracted from the resinous glands. The *Cannabis* plant also contains a cannabinoid called cannabidiol ("CBD"). Cannabis essential oil is usually obtained by separating the resins from the cannabis flowers. Currently, cannabis essential oil is based on being "THC driven" and there is no cannabis essential oil combo for prophylaxis.

Condoms, can be dry, tear, or fall off during use. Condoms can reduce sensitivity during sexual activity, which can make sex stressful and not enjoyable, thereby leading couples to practice unsafe sex, i.e., not use condoms, and increase the risk of spreading sexually transmitted infections and getting pregnant. The cannabis essential oil combo adding in THC brings back added sensitivity with prophylaxis use.

Currently, there exists a condom consisting of a biocompatible polymer or biocompatible material or composition incorporating cannabis or cannabis derived compositions for forming at least part of the structure of a condom useful for preventing sexually transmitted infections. The cannabis or cannabis derived compositions are incorporated within or applied as a coating or coatings to any material suitable for a condom. In other words, the material/composition is not separate from the condom. Furthermore, the material/composition does not comprise "THC driven" cannabis essential oils.

Currently, there exists an herbal emulsion including CBD but very small to no traces of THC. The reason for increase traces of CBD but very little to no traces of THC is because CBD relaxes smooth muscles and causes a very mild increase in sensation while THC enhances skin sensitivity and causes little to no relaxation in muscle. This essential oil is used to make the climax stronger by delaying the climax and allowing the user to time the user's climax with their partner's climax.

Currently, there exist cosmetic or dermatological compositions combining a substance of cannabis essential oil; however, free of cannabinoids since cannabinoids are lipophilic and are virtually insoluble in water. In this composition, there is a combination of cannabis essential oil substantially free of cannabinoids and helichrysum essential oil.

Currently, there also exists a spray containing a blend of whole plant extracts of hemp Kava Kava, cinnamon, ginger, terpenes; however, this spray is incompatible with condoms.

Accordingly, there is a need for an essential oil that can provide increase sensitivity and health benefits during sexual activity, i.e., have THC and very low traces to no CBD. There is a further need for the essential oil to be compatible with a condom to prevent the spread of sexually transmitted infections and pregnancy while also providing an enjoyable experience using an essential oil. Similarly, there is a need for a composition, such as a lubricant to have higher traces of THC and lower traces of CBD comprising essential oil that can provide increase sensitivity and health benefits during sexual activity. Additionally, there is a need for a composition, such as a water-based lubricant comprising an essential oil to be compatible/accessible with condoms. There is also a need for a composition, such as a silicone-based lubricant comprising an essential oil to be compatible/accessible with condoms.

SUMMARY

An object of the present invention is to provide a composition compatible with contact to a skin surface comprising a cannabis essential oil and a water component; the cannabis essential oil comprising a pharmaceutically effective amount of THC, the composition being compatible with a prophylactic.

An object of the present invention is to provide a kit comprising a prophylactic and a cannabis essential oil and a water component; the cannabis essential oil comprising a pharmaceutically effective amount of THC.

Yet another object of the present invention is to provide a packet having at least two chambers, one chamber stores a composition comprising a cannabis essential oil and a water component; the cannabis essential oil comprising a pharmaceutically effective amount of THC and a second chamber stores a prophylactic.

According to an embodiment of the present invention, there is a composition compatible with contact to a skin surface comprising a cannabis essential oil and a water component. The cannabis essential oil comprises a pharmaceutically effective amount of THC. The pharmaceutically effective amount of THC is in an amount between about 20% w/w and about 60% w/w.

According to yet another embodiment of the present invention, there is a kit comprising a composition compatible with contact to a skin surface comprising a cannabis essential oil and a water component and a condom. The cannabis essential oil comprises a pharmaceutically effective amount of THC.

According to another embodiment of the present invention, there is a kit comprising a condom and a composition compatible with contact to a skin surface comprising a cannabis essential oil and a water component, the cannabis essential oil comprising a pharmaceutically effective amount of THC. The condom is stored separately from the composition in a packet, the packet comprising two separate chambers, each chamber separable by a perforated portion of the packet. Each chamber is sealed from the other chamber.

According to another embodiment of the present invention, there is a packet having at least two adjacent chambers, each chamber separable along a perforated portion. There is a first chamber comprising a composition compatible with contact to a skin surface, the composition comprising a cannabis essential oil and a water component; the cannabis essential oil comprising a pharmaceutically effective amount of THC; and a second chamber comprising a prophylactic.

These features, advantages and other embodiments of the present invention are further made apparent, in the remainder of the present document, to those of ordinary skill in the art.

BRIEF DESCRIPTION OF THE DRAWINGS

In order to more fully describe embodiments of the present invention, reference is made to the accompanying drawings. These drawings are not to be considered limitations in the scope of the invention, but are merely illustrative.

DETAILED DESCRIPTION OF SPECIFIC EMBODIMENTS

Figure 1:
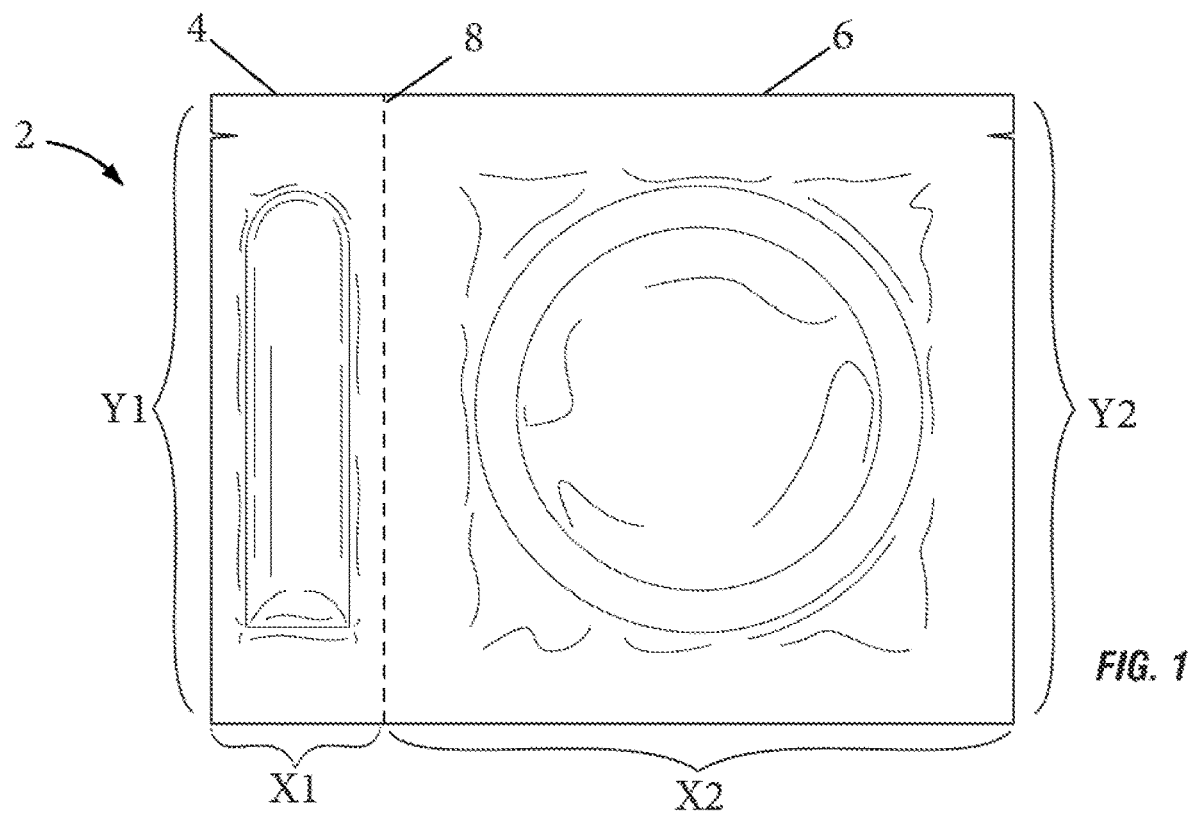
FIG. 1 illustrates a front view of a packet comprising two chambers for storing a composition comprising a therapeutically effective amount of cannabis essential oil and a prophylactic, according to an embodiment of the present invention.

The description above and below and the drawings of the present document focus on one or more currently preferred embodiments of the present invention and also describe some exemplary optional features and/or alternative embodiments. The description and drawings are for the purpose of illustration and not limitation. Those of ordinary skill in the art would recognize variations, modifications, and alternatives. Such variations, modifications, and alternatives are also within the scope of the present invention. Section titles are terse and are for convenience only.

The terms "sufficient" and "effective", as used interchangeably herein, refer to an amount (i.e. mass, volume, dosage, concentration, and/or time period) needed to achieve one or more desired result(s). In an embodiment, an effective amount of cannabis essential oil refers to an amount needed to achieve one or more therapeutic effects. In an embodiment, an effective amount of THC or pharmaceutically effective amount of THC refers to an amount needed to achieve one or more therapeutic effects. A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for human pharmaceutical use. "A pharmaceutically acceptable excipient, diluent, carrier and/or adjuvant" as used in the specification and claims includes one and more such excipients, diluents, carriers, and adjuvants.

The term "therapeutically effective amount" as used herein refers to that amount of an embodiment of the composition being administered that will stimulate/make sensitive the user during intimate relations. In an embodiment, a therapeutically effective amount of THC refers to an amount needed to achieve one or more therapeutic effects.

As used herein, a "composition" or a "formulation" is meant to encompass a composition suitable for administration to a subject, such as a mammal, especially a human and that refers to the combination of an active agent(s) (e.g., THC), or ingredient with a pharmaceutically acceptable carrier or excipient, making the composition suitable for diagnostic, therapeutic, or preventive use in vitro, in vivo, or ex vivo. In general a "composition" is sterile, and preferably free of contaminants that are capable of eliciting an undesirable response within the subject (e.g., the compound(s) in the composition is pharmaceutical grade). Compositions can be designed for administration to subjects or patients in need thereof via a number of different routes of administration.

The present invention provides a new composition comprising a therapeutically effective amount of cannabis essential oil. The composition comprising a therapeutically effective amount of cannabis essential oil can be in a solid, semisolid or liquid formulation. In a solid formulation, the composition comprising a therapeutically effective amount of cannabis essential oil can be in the form of a tablet, capsule pellets, or powder. In a liquid or semisolid formulation, the composition can be in the form of exilirs, suspension, or emulsion. When the composition comprising a therapeutically effective amount of cannabis essential oil is applied to an area of the body for direct treatment, i.e., topical application, the composition can be in the form of drops, creams, ointments, pastes, gels or lotions. The drops are either aqueous or oily suspensions. The creams can have an aqueous base and the ointments can be lipid base. The pastes can have powder and the gels and lotions can be alcoholic based. For transdermal administration of the composition comprising a therapeutically effective amount of cannabis essential oil, the composition can be in the form of a patch, gel or spray. For rectal or vaginal administration, the composition can be in the form of a suppository, enema, or pessary.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7.sup.th ed., Lippincott, Williams, & Wilkins; and Handbook of Pharmaceutical Excipients (2000) A. H. Kibbe et al., eds., 3.sup.rd ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public. In pharmaceutical dosage forms, the composition may be administered in the form of its pharmaceutically acceptable salts, or a subject active composition may be used alone or in appropriate association, as well as in combination, with other pharmaceutically active compounds. The following methods and excipients are merely exemplary and are in no way limiting. All percentages and amounts in the present application, if not otherwise defined, are to be defined as weight percents (w/w).

One embodiment of the present invention is a water-based lubricant. Another embodiment of the present invention is a silicone-based lubricant. However, other formulations as mentioned above can be contemplated. Both embodiments of lubricants comprise a composition comprising a therapeutically effective amount of cannabis essential oil. The present invention is also directed to the use of THC as the active ingredient in the composition as THC is known for causing increased sensation, providing a euphoric feeling in the tissue lining of contact and for having very little effect on muscle relaxation. In the present invention, trace amounts of CBD is found as CBD is known for blocking the effects of THC, relaxing smooth muscles and very mildly increasing sensation.

The present invention is also directed to a kit comprising the composition comprising a therapeutically effective amount of cannabis essential oil and a prophylactic. The prophylactic can be a condom or other types of disease/pregnancy preventive measure. By having a kit, the user will find both the composition comprising a therapeutically effective amount of cannabis essential oil and prophylactic accessible at the same time encouraging the use of enjoyable, safe sex.

The present invention is also directed to the packet of the composition comprising a therapeutically effective amount of cannabis essential oil. The packet comprises at least two chambers separated by a perforated portion. Each chamber is individually sealed from the other chamber. In an embodiment, the chambers are hermetically sealed from one another. The chamber storing the composition can be removed along the perforated portion and then opened or both chambers can be opened at once. The second chamber can store a condom or another type of prophylactic.

A composition comprising a therapeutically effective amount of cannabis essential oil is compatible with prophylactics, i.e., condoms. Cannabis essential oil can provide the proper lubricant needed for users of condoms while also be compatible with condoms. The cannabis essential oil used according to the present invention comprises a much higher THC content and minimal traces of CBD content. This is because THC provides positive properties to the tissue lining of contact such, as the vaginal wall because THC increases sensitivity during sexual activity. In an embodiment of the present invention, the therapeutically effective amount of cannabis essential oil in the composition comprises at least 5 milligrams of THC. The range of THC can be from 5 mg to 15 mg depending on the cannabis essential oil used in the composition. Preferably, the THC concentration in an embodiment of the present invention is about 20% w/w to about 60% w/w THC and the preferred range of trace amounts of CBD is 2% w/w or less.

To illustrate, a concentration range of "about 0.1% w/w to about 5% w/w" should be interpreted to include not only the explicitly recited concentration of about 0.1% w/w to about 5% w/w, but also include individual concentrations (e.g., 1% w/w, 2% w/w, 3% w/w, and 4% w/w) and the sub-ranges (e.g., 0.5% w/w, 1.1% w/w, 2.2% w/w, 3.3% w/w, and 4.4% w/w) within the indicated range. In an embodiment, the term "about" can include traditional rounding according to significant figures of the numerical value. In addition, the phrase "about 'x' to 'y'" includes "about 'x' to about 'y'". "Water-based component" and "water component" have the same meaning.

The water-based component of the present invention comprises a mixture of water and a source selected from a group such as Aloe Vera, hemp, cornstarch, egg whites, flax, and almond extract. Hemp is the fiber and see part of the *Cannabis sativa* L. plant. Flax is a blue-flowered herbaceous plant that is cultivated for its seed (linseed). Pure almond extract is made from three primary ingredients: alcohol, water, and bitter almond oil; however, a combination of the alcohol, water, and bitter almond oil or a removal of at least one of these components can be done to create the water-based component of the present invention. The array of sources for the water-based component makes the lubricant biocompatible for users with varying allergies. The lubricant comprises about 35% w/w to about 55% w/w water and about 45% w/w to about 65% w/w cannabis essential oil, preferably about 40% w/w water and about 60% w/w cannabis essential oil. Therefore the percentage of the Aloe Vera, hemp, cornstarch, egg whites, flax, or almond extract is about 35% w/w to about 55% w/w of the lubricant. However, other ranges and percentages of water to a therapeutically effective amount of cannabis essential oil can be contemplated. The above mentioned water-based lubricant can also be organic or natural, i.e. from agriculture conducted according to certain standards, such as the use of stated methods of fertilization and pest control.

Silicone-based lubricant comprising namely a therapeutically effective amount of cannabis essential oil is another embodiment of the present invention. Silicone-based lubricants feel differently from water-based lubricants and are not absorbed by skin or mucous membranes. In an embodiment of the present invention, the therapeutically effective amount of cannabis essential oil comprises at least 5 mg of THC. The range of the therapeutically effective amount of THC can be from 5 mg to 15 mg depending on the cannabis essential oil used in the composition. Preferably, the therapeutically effective amount of THC concentration in an embodiment of the present invention is about 20% w/w to about 60% w/w THC and the preferred range of trace amounts of CBD is 2% w/w or less. The lubricant comprises about 35% w/w to about 55% w/w silicone and about 45% w/w to about 65% w/w cannabis essential oil, preferably about 40% w/w silicone and about 60% w/w cannabis essential oil.

One method for making the water-based component comprises about a 1:12 ratio of cornstarch to water. Once the water and cornstarch are mixed, bring the mixture slowly to a boil on low to medium heat, stirring frequently for about 30 seconds. Another method for making the water-based component comprises using 100% w/w pure Aloe Vera containing no gels with alcohol. The 100% w/w pure Aloe Vera can be found at most pharmacies or from an Aloe Vera plant.

The present invention provides a novel packet 2 for storing the composition comprising a therapeutically effective amount of cannabis essential oil. As illustrated in FIG. 1, the packet 2 comprises at least two chambers, the first chamber 4 stores the composition comprising a therapeutically effective amount of cannabis essential oil and the second chamber 6 has the option to store a prophylactic such as a condom. The first chamber 4 is about ¾ inches wide (labeled "X1") and about 2½ inches to 2¾ inches long (labeled "Y1"). The second chamber 6 can range from about 2½ inches to 2¾ inches wide (labeled "X2") and about 2½ inches to 2¾ inches long (labeled "Y2"). The first chamber 4 and second chamber 6 are separate to prevent the composition comprising a therapeutically effective amount of cannabis essential oil from touching the other object for a long period of time. Each chamber is individually sealed from the other chamber. The composition comprising a therapeutically effective amount of cannabis essential oil is single use. The first chamber 4 and second chamber 6 can be torn apart by tearing along the perforated portion 8 on the packet 2, such that the first chamber 4 and second chamber 6 are separated yet each chamber remains sealed (i.e. chambers are separated without the chamber being opened). The perforated portion 8 can be located anywhere on the packet 2, preferably along the Y length of the packet 2. The packet 2 can also be hermetically sealed. In an embodiment, the chambers are hermetically sealed from one another. The packet 2 allows the lubricant to stay clean yet accessible.

Figure 2:
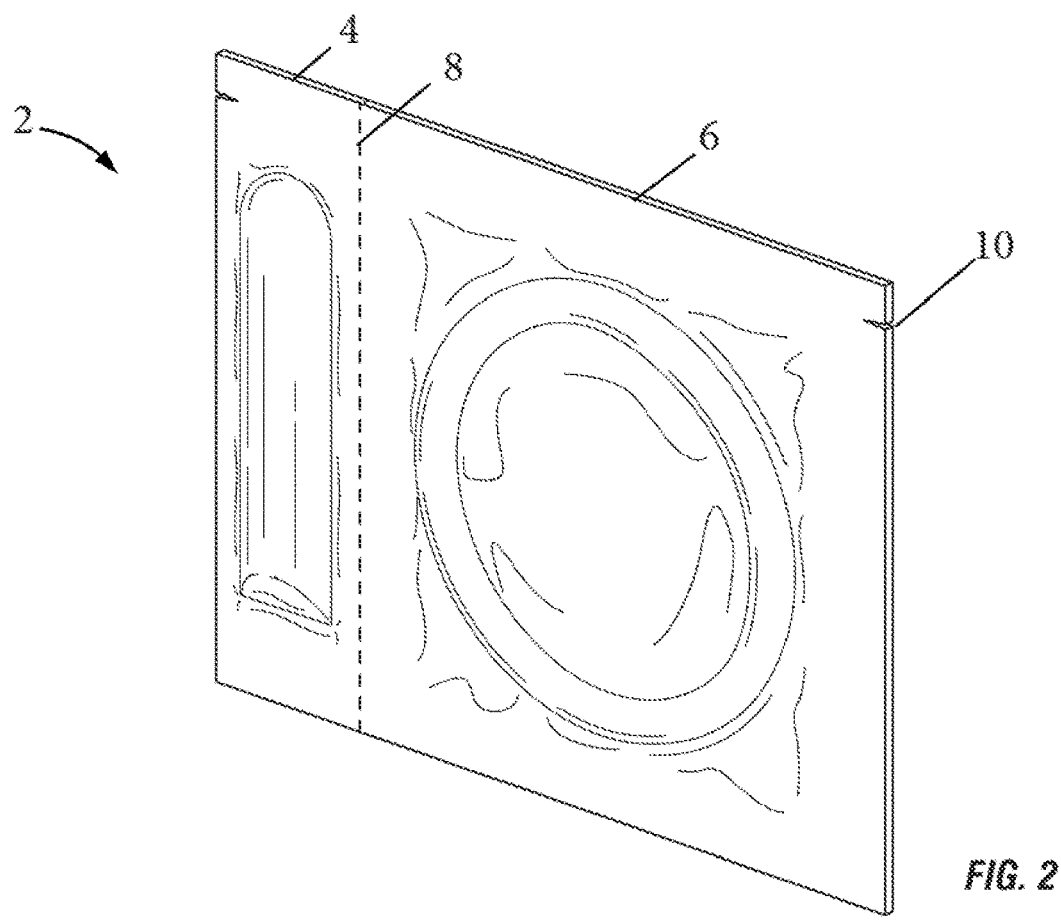
FIG. 2 illustrates a perspective view of a closed packet comprising two chambers for storing a composition comprising a therapeutically effective amount of cannabis essential oil and a prophylactic, according to an embodiment of the present invention.

FIG. 2 illustrates a perspective view of a closed packet 2 comprising two chambers for storing a composition comprising a therapeutically effective amount of cannabis essential oil and prophylactic, according to an embodiment of the present invention. The first chamber 4 comprises the composition comprising a therapeutically effective amount of cannabis essential oil and the second chamber 6 comprises the prophylactic. The packet 2 has a tear away portion 10 making it easier for the user to open the packet 2 from either the first chamber 4 or from the second chamber 6. By keeping the prophylactic and composition comprising a therapeutically effective amount of cannabis essential oil separate in its individual chamber, the composition and prophylactic will last longer. FIG. 2 illustrates the compact style of the packet 2. As mentioned previously, the packet 2 can comprise more than two chambers in other embodiments.

Figure 3:
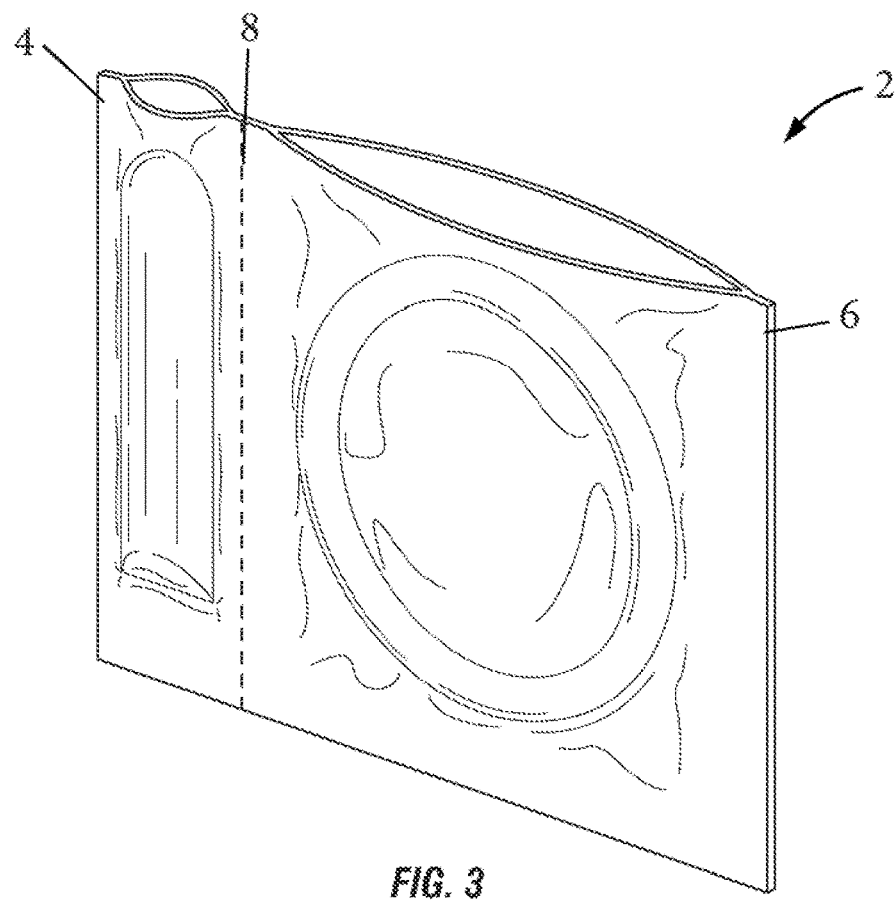
FIG. 3 illustrates a perspective view of an open packet comprising two chambers for storing a composition comprising a therapeutically effective amount of cannabis essential oil and a prophylactic, according to an embodiment of the present invention.

FIG. 3 illustrates a perspective view of an open packet 2 comprising two chambers for storing a composition comprising a therapeutically effective amount of cannabis essential oil and prophylactic, according to an embodiment of the present invention. The first chamber 4 stores the composition comprising a therapeutically effective amount of cannabis essential oil and the second chamber 6 stores the prophylactic. As illustrated, both the first chamber 4 and the second chamber 6 can be open at once. However, if the first chamber 4 is to be opened first, the composition comprising a therapeutically effective amount of cannabis essential oil is applied and then the second chamber 6 can be opened before prophylactic use.

Figure 4:
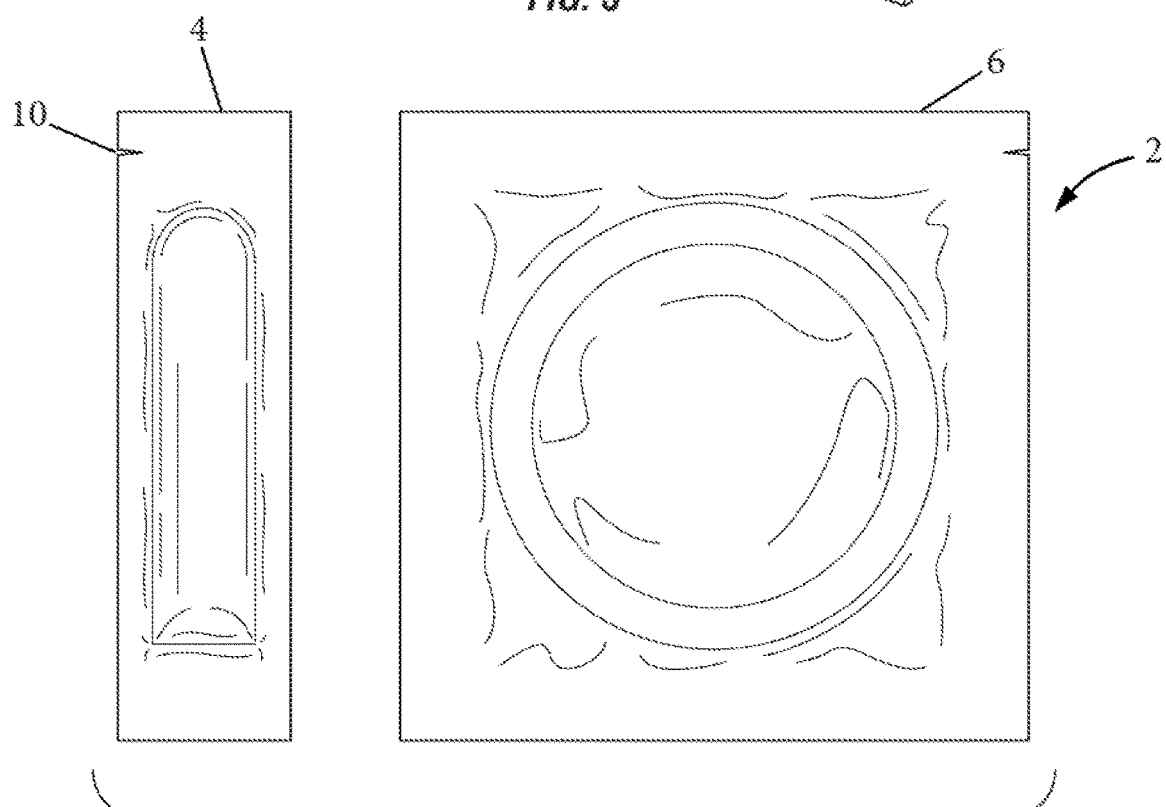
FIG. 4 illustrates a front view of the two chambers separated along the perforated portion, according to an embodiment of the present invention.

FIG. 4 illustrates a front view of the two chambers separated along the perforated portion (not shown, see FIG. 3), according to an embodiment of the present invention. The first chamber 4 and the second chamber 6 are separated without being open along the tear away portion 10. In this case, if the user is not ready to use either the composition comprising a therapeutically effective amount of cannabis essential oil or prophylactic and wants to save either for later use, the user can simply tear along the perforated portion to separate the first chamber 4 from the second chamber 6.

A method of using the present invention comprises opening the packet 2, wearing the latex condom; then applying the composition comprising a therapeutically effective amount of cannabis essential oil onto the outside surface of the condom and waiting approximately 12 minutes before intercourse. Another method comprises: opening the packet 2, applying the composition comprising a therapeutically effective amount of cannabis essential oil comprising cannabis essential oil directly on the targeted skin surface; waiting approximately 12-20 minutes for the composition to absorb, and wearing the condom before intercourse. The user has the flexibility of separating the first chamber 4 from the second chamber 6 by tearing along the perforated portion 8 and saving either the condom or the composition for later use without contaminating it. Either way, having the first chamber 4 and second chamber 6 originally attached makes the condom and lubricant readily accessible.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments or alternatives of the foregoing description.

What is claimed is:

1. A kit comprising
a composition compatible with contact to a skin surface comprising a cannabis essential oil and a water component, wherein the water component is a mixture of water and an ingredient selected from the group consisting of cornstarch, egg whites, flax, and a combination thereof, the cannabis essential oil comprising a pharmaceutically effective amount of THC; and
a condom stored separately from the composition in a packet, the packet comprising two separate chambers, each chamber separable by a perforated portion of the packet.

2. The kit of claim 1, wherein the water component is in an amount between about 35% w/w and about 55% w/w.

3. The kit of claim 2, wherein the water component is in an amount preferably about 40% w/w.

4. The kit of claim 1, wherein the cannabis essential oil is in an amount between about 45% w/w and about 65% w/w.

5. The kit of claim 1, wherein the pharmaceutically effective amount of THC is in an amount between about 20% w/w and about 60% w/w.

6. The kit of claim 1, wherein the water component is organic.

7. A packet having at least two adjacent chambers, each chamber separable along a perforated portion, the packet comprising:
a first chamber, of the two adjacent chambers, comprising a composition compatible with contact to a skin surface, the composition comprising a cannabis essential oil and a water component, wherein the water component is a mixture of water and an ingredient selected from the group consisting of cornstarch, egg whites, flax, and a combination thereof; and the water component is in an amount between about 35% w/w and about 55% w/w; the cannabis essential oil comprising a pharmaceutically effective amount of THC; and
a second chamber, of the two adjacent chambers, comprising a prophylactic.

8. The packet of claim 7, wherein the prophylactic is a condom.

9. The packet of claim 7, wherein the adjacent chambers are individually sealed within the packet, each chamber is separable from another chamber without opening either chamber.

10. The packet of claim 7, wherein the cannabis essential oil is in an amount between about 45% w/w and about 65% w/w; and
the pharmaceutically effective amount of THC is in an amount between about 20% w/w and about 60% w/w.

* * * * *